(12) United States Patent
Chin et al.

(10) Patent No.: US 11,000,031 B2
(45) Date of Patent: May 11, 2021

(54) SYSTEM AND METHOD FOR ELECTROPHORETIC DECELLULARIZATION

(71) Applicant: Fabrico, Inc., Austin, TX (US)

(72) Inventors: Robert C. Chin, Austin, TX (US); Leonid Bunegin, San Antonio, TX (US)

(73) Assignee: FABRICO TECHNOLOGY INC, Georgetown, TX (US)

( * ) Notice: Subject to any disclaimer, the term of this patent is extended or adjusted under 35 U.S.C. 154(b) by 0 days.

(21) Appl. No.: 15/978,134

(22) Filed: May 12, 2018

(65) Prior Publication Data

US 2018/0325102 A1 Nov. 15, 2018

Related U.S. Application Data

(60) Division of application No. 14/242,807, filed on Apr. 1, 2014, now abandoned, which is a continuation of application No. PCT/US2012/000508, filed on Oct. 3, 2012.

(60) Provisional application No. 61/542,665, filed on Oct. 3, 2011.

(51) Int. Cl.
 *A01N 1/02* (2006.01)
 *A61L 27/36* (2006.01)
 *C12N 1/06* (2006.01)

(52) U.S. Cl.
 CPC ........ *A01N 1/0294* (2013.01); *A61L 27/3691* (2013.01); *C12N 1/066* (2013.01)

(58) Field of Classification Search
 CPC .... A01N 1/0294; A61L 27/3691; C12N 1/066
 See application file for complete search history.

(56) References Cited

U.S. PATENT DOCUMENTS

| | | | | |
|---|---|---|---|---|
| 2003/0009100 | A1* | 1/2003 | Derendorf | A61B 5/145 600/424 |
| 2003/0087428 | A1* | 5/2003 | Wolfinbarger, Jr. | A61K 35/32 435/325 |
| 2005/0107817 | A1* | 5/2005 | White | A61M 25/00 606/191 |
| 2007/0020248 | A1* | 1/2007 | Everaerts | A61K 35/34 424/93.21 |
| 2009/0269317 | A1* | 10/2009 | Davalos | A61K 35/12 424/93.7 |

\* cited by examiner

*Primary Examiner* — William H. Beisner
*Assistant Examiner* — Danielle B Henkel (57) ABSTRACT

A method of decellularizing a tissue includes disposing the tissue within a device, the device. The device includes a container, first and second electrodes disposed within the container and defining a space between the first and second electrodes to receive the tissue, a perfusion pump, and a conduit connected to the perfusion pump to transport a decellularization composition from the pump into the tissue. The method further includes disposing the decellularization composition within the container to surround the tissue and contact the first and second electrodes, applying an electric potential across the first and second electrodes, and perfusing the decullarization composition into the tissue.

20 Claims, 6 Drawing Sheets

165 Hours

279 Hours

329 Hours

401 Hours

425 Hours

470 Hours

FIG. 11

SYSTEM AND METHOD FOR ELECTROPHORETIC DECELLULARIZATION

CROSS-REFERENCE TO RELATED APPLICATION(S)

This application is a divisional of U.S. patent application Ser. No. 14/242,807, filed Apr. 1, 2014, which is a continuation of PCT Application No. PCT/US2012/000508, filed Oct. 3, 2012, entitled "SYSTEM AND METHOD FOR ELECTROPHORETIC DECELLULARIZATION," which claims benefit of U.S. Provisional Application No. 61/542,665, filed Oct. 3, 2011, entitled "SYSTEM AND METHOD FOR ELECTROPHORETIC DECELLULARIZATION," each of which is incorporated herein by reference in its entirety.

FIELD OF THE DISCLOSURE

This disclosure, in general, relates to systems and methods for electrophoretic decellularization of tissue and tissue formed by such methods and systems.

BACKGROUND

Despite the life saving use of transplants, the demand for donor organs continues to be significant. Such demand has outstripped the availability of reliable sources for these organs. Thus, to satisfy this burgeoning demand, alternative transplant technologies are being developed, which can provide patient specific organs on demand. Likewise, worldwide musculoskeletal injuries and degeneration represent the most common cause of pain and suffering. When portions of muscle or skin are lost, normal function around the joint that the muscle and tendons controls is limited or lost. Such injuries may be permanently debilitating Advances in tissue engineering and stem cell research promise future treatments that may produce portions of or even complete muscles, tissues or organs. Tissue engineering for a number of tissues is now entering clinical practice.

The field of tissue engineering is dedicated to developing a range of new solutions including refined rotational grafts of donor tissue, innovative injection of growth factors and the use of regenerative stem cell therapy. Current development of bio-scaffolds for muscle, tissue or organ regeneration has focused on polymer biochemistry and natural and synthetic collagen type materials. The drawback of such synthetic biochemical polymer scaffolds is the difficult task of fabricating a biomaterial which is biocompatible with low immunogenicity, is capable of inducing endogenous progenitor cells, is structurally sound, and can have the biomechanical integrity of real tissue, while being biodegradable as the new tissue or organ regenerates and replaces the implanted scaffold. Further, a desirable replacement tissue possesses a complicated vascular architecture to support and supply blood flow and innervation.

Current treatment options have limited and less than satisfactory outcomes including permanent functional disfigurement, loss of muscle function and poor quality of life. Currently, no treatment is available to regenerate large volumes of muscle, tissue and organs. Such limited regenerative treatments are driving military and civilian healthcare providers to find alternative methods to reconstructive surgery and organ transplantation.

SUMMARY

In a first aspect, a device for decellularizing a tissue includes a container, first and second electrodes disposed within the container and defining a space between the first and second electrodes to receive the tissue, a perfusion pump, and a conduit connected to the perfusion pump to transport a decellularization solution from the pump into the tissue.

In a second aspect, a method of decellularizing a tissue includes disposing the tissue within a device. The device includes a container, first and second electrodes disposed within the container and defining a space between the first and second electrodes to receive the tissue, a perfusion pump, and a conduit connected to the perfusion pump to transport a decellularization composition from the pump into the tissue. The method further includes disposing the decellularization composition within the container to surround the tissue and contact the first and second electrodes, applying an electric potential across the first and second electrodes, and perfusing the decellularization composition into the tissue.

In a third aspect, a device for decellularizing a tissue includes a container, first and second electrodes disposed within the container and defining a space between the first and second electrodes to receive the tissue, the first and second electrodes including a surface of a corrosion-resistant conductive material, and a tissue support to position the tissue within the space.

In a fourth aspect, a method of decellularizing a tissue includes disposing the tissue within a device. The device includes a container, first and second electrodes disposed within the container and defining a space between the first and second electrodes to receive the tissue, the first and second electrodes including a surface of a corrosion-resistant conductive material, and a tissue support to position the tissue within the space. The method further includes disposing a decellularization composition within the container to surround the tissue and contact the first and second electrodes and applying an electric potential across the first and second electrodes.

In a fifth aspect, a method of decellularizing a tissue includes disposing the tissue within a device. The device includes a container, first and second electrodes disposed within the container and defining a space between the first and second electrodes to receive the tissue, and a tissue support to position the tissue within the space. The method further includes disposing a decellularization composition within the container to surround the tissue and contact the first and second electrodes, the decellularization composition buffered to a pH in a range of 6.5 to 8.5, and applying an electric potential across the first and second electrodes.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

In an embodiment, an electrophoretic decellularization device includes a container, at least two electrodes disposed within the container, and a tissue support disposed in a space defined between the at least two electrodes. The electrodes can be coupled to a power supply, which can provide a voltage difference between the electrodes that is static, oscillating, or combination thereof. In an example, one of the electrodes has a surface facing the opposite electrode, the surface area of the electrode being at least 60% of the projected area of a tissue sample disposed between the electrode and the opposite electrode. In another example, the electrode is coated with a corrosion-resistant conductive material, such as a corrosion-resistant metal, ceramic, polymer, or combination thereof. A decellularization composition can be disposed within the container and in contact with the electrodes and the tissue sample. In a particular example, the solution is buffered to have a desirable pH of greater than 6.0, such as a pH in a range of 6.5 to 8.5. In an example, the decellularization composition is an ionic solution, such as a saline solution. In another example, the decellularization composition is a hydrogel. Further, the system can include a perfusion pump and a conduit to connect with tissue and provide the decellularization composition into the tissue.

In another embodiment, a method of decellularizing tissue includes placing a tissue sample in an electrophoretic decellularization device, such as the device described above, applying a decellularization composition into the container in contact with the electrodes and a tissue sample, and applying a voltage difference across the electrodes. In an example, the decellularization composition can be perfused into the tissue sample, for example, using an injection needle or existing vascular structures. Optionally, the decellularized tissue sample can be washed, treated, and repopulated with cells.

Figure 1:
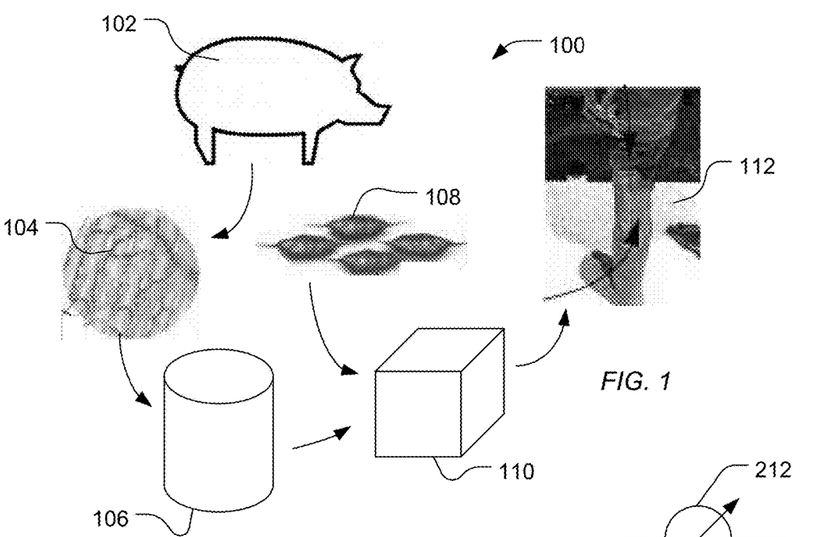
FIG. 1 includes an illustration depicting the process flow for generating replacement tissue.

As illustrated in the process 100 of FIG. 1, a tissue 104 is derived from a donor 102. In an example, the donor 102 is a patient. In another example, the donor is an allogeneic or a xenogeneic donor. The tissue sample 104 can be muscle tissue, bone, vascular tissue, organ tissue, ligaments, tendons, nerve tissue, brain tissue, cartilage, ureter tissue, bladder tissue, or any combination thereof. In particular, the tissue sample 104 can be a muscle tissue, such as skeletal muscle tissue, heart muscle tissue, heart valve tissue, intestinal tissue, or any combination thereof. In another example, the tissue sample 104 can be an organ tissue, such as liver tissue, kidney tissue, pancreatic tissue, epidermal tissue, arterial or vascular tissue, nerve tissue, brain tissue, or any combination thereof.

Optionally, the tissue 104 can be pretreated, exposing the tissue 104 to a hypotonic or hypertonic solution, a surfactant solution, buffers, protease inhibitors, enzymatic treatment, a wash solution, or any combination thereof.

The tissue sample 104 is treated in an electrophoretic decellularization device 106. Such an electrophoretic decellularization device 106 removes cellular material from the tissue sample 104, leaving an extracellular matrix (ECM). The electrophoretic decellularization device 106 includes a container, at least two electrodes, and a tissue support. A decellularization composition is placed along with the tissue sample in the electrophoretic decellularization device 106. The decellularization composition is in contact with the electrodes and the tissue sample. A voltage potential is applied across the electrodes, and cellular material is removed from the tissue sample, leaving the extracellular matrix (ECM). In addition, the decellularization composition can be perfused into the tissue using existing vascular structures or using needles. Following decellularization, the ECM can be washed or can be pretreated with agents to enhance growth, such as growth factors, cytokines such as chemokines, PEGylated fibrinogen, or any combination thereof.

Optionally, the extracellular matrix (ECM) is transferred to a regeneration device 110, along with cells 108, to repopulate the ECM in vitro. The cells 108 can be differentiated cells specific to the desired tissue type. In another example, the cells 108 are stem cells. The stems cells can be totipotent, pluripotent, mulitpotent, oligopotent, or unipotent stem cells, and can be derived from zygote, embryonic, or adult sources. In particular, bone marrow mesenchymal cells can be used either in vitro or in vivo to repopulate an ECM. The cells 108 repopulate the extracellular matrix (ECM), generating replacement tissue. The replacement tissue may be implanted in a patient 112. Alternatively, the extracellular matrix (ECM) can be implanted in the patient 112 without the application of cells 108.

Figure 2:
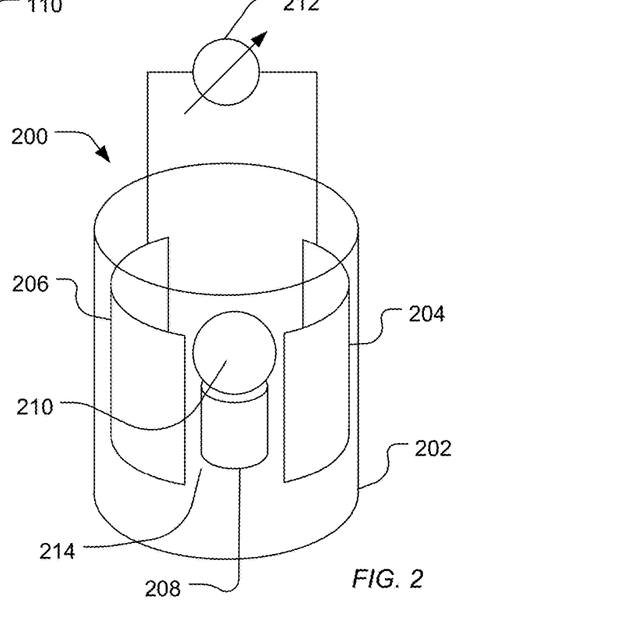
FIG. 2 includes an illustration of an exemplary electrophoretic decellularization device.

As illustrated in FIG. 2, an electrophoretic decellularization device 200 includes at least two electrodes 204 and 206 disposed in a container 202. A tissue sample 210 is placed on a tissue holder 208 to secure the tissue sample 210 between the electrodes 204 and 206. An electric potential is provided across the electrodes 204 or 206, such as by a power source 212. Further, a decellularization composition 214 is placed within the container 202 in contact with the electrodes 204 or 206 and the tissue sample 210.

In an example, one or more of the electrodes 204 or 206 is formed of or coated with a corrosion-resistant conductive material. In example, the corrosion-resistant conductive material includes a metal, a ceramic material, a conductive polymeric material, or any combination thereof. An exemplary corrosion-resistant conductive metal includes platinum, gold, silver, or any combination thereof. An exemplary ceramic conductive material includes indium tin oxide, tungsten silicide, tantalum nitride, indium oxide, tungsten nitride, titanium nitride, titanium diboride, molybdenum silicide, silicon carbide, zirconia, tin oxide, lanthanum chromite, doped alumina, or any combination thereof. An exemplary conductive polymeric material includes polyacetylene, poly(p-phenylene vinylene), polyfluorene, polyphenylene, polypyrene, polyazulene, polynaphthalene, polypyrrole, polycarbazole, polyindole, polyazepine, polyaniline, polythiophene, poly(3,4-ethylenedioxythiophene, poly(p-phenylene sulfide), or any combination thereof. In another example, the corrosion-resistant conductive material can include a conductive composite material including conductive particles in a polymeric matrix.

In an example, each of the electrodes 204 or 206 is formed of or coated with the same corrosion-resistant conductive material. Alternatively, the electrodes 204 or 206 can be formed of or coated with different corrosion-resistant conductive materials.

As illustrated in FIG. 2, the power source 212 is coupled to the electrode 204 and the electrode 206. In an example, the power source 212 provides a constant potential or voltage difference between the electrodes 204 or 206. In another example, the power source 212 provides an oscillating voltage difference between the electrodes 204 or 206, such as an alternating voltage difference between the electrodes 204 or 206. In a further example, the power source 212 can provide an oscillating voltage difference with a voltage bias between the electrodes 204 or 206. In particular, the power source 212 can supply a voltage difference in a range of 0.1 V to 200 V, such as a range of 1 V to 100 V, a range of 5 V to 90V, or even a range of 10 V to 60 V. Further, the power supply 212 can provide a current in a range of 0.05 amps to 5 amps, such as a range of 0.1 amps to 3 amps, a range of 0.1 amps to 2 amps, or even a range of 0.5 amps to 1 amp.

Figure 3:
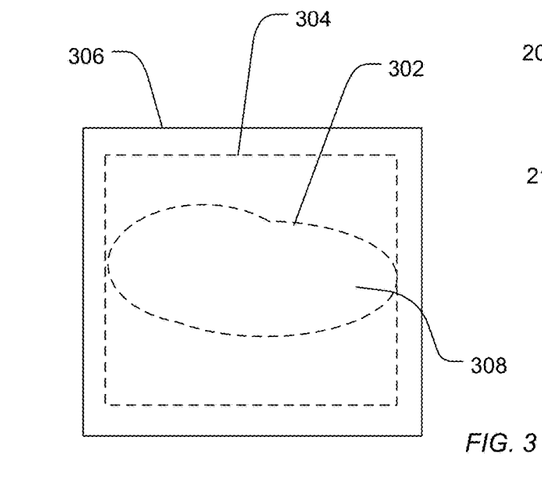
FIG. 3 includes an illustration of an exemplary projection of a tissue sample on an electrode surface.

In an example, the electrodes 204 or 206 have a desirable surface area relative to the size of the projected surface area of the tissue sample 210. When viewing the tissue sample 210 through an electrode toward a different electrode, the tissue sample projects a perimeter, defining a projected area on the electrode. For example, as illustrated in FIG. 3, when viewing a tissue sample through an electrode 306, the tissue sample defines a perimeter 302 surrounding a projected area 308 projected onto the electrode 304 or 306. In particular, the surface area of the electrode 304 or 306 is at least 60% of the projected area of the tissue sample. For example, the surface area of the electrode can be at least 75% of the projected area, such as at least 90% of the projected area, or even at least 100% of the projected area. In a particular example, the surface area can be at least 115%, such as at least 130%, or even at least 150% of the projected area of the tissue sample. In a further example, the container can include physical restrictions, such as baffles, providing an effective cross-sectional area for current or ion flow. Such restrictions can effectively provide the surface area as described above.

Figure 5:
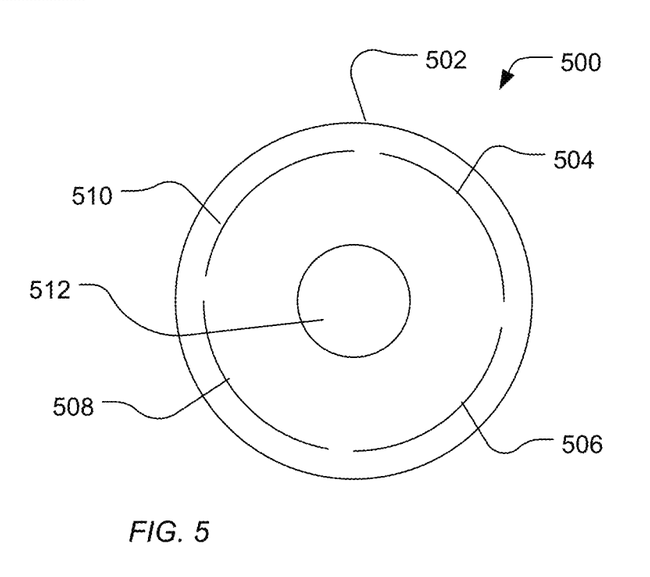
FIG. 5 includes an illustration of an exemplary electrophoretic decellularization device.

In a further example, the tissue holder 208 can rotate the tissue sample 210 by at least 90°. For example, the tissue holder 208 can rotate the tissue sample 210 by at least 180°. Alternatively, the electrodes 204 or 206 can be rotated around the sample by at least 90°, such as at least 180°. In a further alternative example, the electrophoretic decellularization device 200 can include additional electrodes. For example, as illustrated in the top view of FIG. 5, the electrophoretic decellularization device 500 can include at least four electrodes 504, 506, 508, and 510, surrounding a tissue sample 512 in a container 502. Each opposing pair of electrodes can be activated with a relative electric potential that is either constant, oscillating, or both.

Returning to FIG. 2, the space disposed between the electrodes 204 and 206 in which the tissue sample 210 is disposed includes a decellularization composition in contact with the electrodes 204 or 206 and the tissue sample 210. The decellularization composition can be a liquid composition. In an alternative example, the decellularization composition can be a hydrogel composition. For example, the hydrogel can be formed of an agarose gel, a polyacrylate, a polyacrylamide gel, or any combination thereof. In particular, the hydrogel can include 0.1% to 5% (w/v) of an agarose or polymer component.

In an example, the decellularization composition is a buffered composition having a desirable pH in a range of 6.5 to 8.5. For example, the pH of the decellularization composition can be in a range of 7.0 to 8.0. In an example, the decellularization composition is buffered with an agent, such as a carboxylic acid, a phosphate salt such as monopotassium phosphate or diammonium phosphate, or any combination thereof.

Further, the decellularization composition includes a surfactant. For example, the decellularization composition can include a surfactant in an amount of 0.01 wt % to 10 wt %, such as a range of 0.01 wt % to 7 wt %, a range of 0.05 wt % to 5 wt %, or even a range of 0.1 wt % to 5 wt %.

In an example, the surfactant is an ionic surfactant, an amphoteric surfactant, or a non-ionic surfactant. The ionic surfactant can be an anionic surfactant. In another example, the ionic surfactant can be a cationic surfactant. An exemplary anionic surfactant includes a sulfate surfactant, a sulfonate surfactant, a phosphate surfactant, a carboxylate surfactant, or any combination thereof. An exemplary sulfate surfactant includes alkyl sulfates, such as ammonium lauryl sulfate, sodium lauryl sulfate, or a combination thereof; an alkyl ether sulfate, such as sodium laureth sulfate, sodium myreth sulfate, or any combination thereof; or any combination thereof. An exemplary sulfonate surfactant includes an alkyl sulfonate, such as sodium dodecyl sulfonate; docusates such as dioctyl sodium sulfosuccinate; alkyl benzyl sulfonate; or any combination thereof. An exemplary phosphate surfactant includes alkyl aryl ether phosphate, alkyl ether phosphate, or any combination thereof. An exemplary carboxylic acid surfactant includes alkyl carboxylates, such as fatty acid salts or sodium stearate; sodium lauroyl sarcosinate; a bile acid salt, such as sodium deoxycholate; or any combination thereof.

An exemplary cationic surfactant includes primary, secondary or tertiary amines, quaternary ammonium surfactants, or any combination thereof. An exemplary quaternary ammonium surfactant includes alkyltrimethylammonium salts such as cetyl trimethylammonium bromide (CTAB) or cetyl trimethylammonium chloride (CTAC); cetylpyridinium chloride (CPC); polyethoxylated tallow amine (POEA); benzalkonium chloride (BAC); benzethonium chloride (BZT); 5-bromo-5-nitro-1,3-dioxane; dimethyldioctadecylammonium chloride; dioctadecyldimethylammonium bromide (DODAB); or any combination thereof.

An exemplary amphoteric surfactant includes a primary, secondary, or tertiary amine or a quaternary ammonium cation with a sulfonate, carboxylate, or phosphate anion. An exemplary sulfonate amphoteric surfactant includes (3-[(3-cholamidopropyl)dimethylammonio]-1-propanesulfonate); a sultaine such as cocamidopropyl hydroxysultaine; or any combination thereof. An exemplary carboxylic acid amphoteric surfactant includes amino acids, imino acids, betaines such as cocamidopropyl betaine, or any combination thereof. An exemplary phosphate amphoteric surfactant includes lecithin. In a further example, the surfactant can be a non-ionic surfactant such as a polyethylene glycol-based surfactant.

In particular, the decellularization composition can be provided by perfusion through the vascular system of the organs. For example, the decellularization device can include a perfusion pump and one or more tubes or needles to perfuse the decellularization composition into the tissue sample. Absent a vascular system (muscle or tissue), the decellularization composition can be supplied using a circulation of the reagents in the chamber or by direct injection into the tissue using a needle or cannula Any of the circulation method, the direct injection method, or the perfusion method can be performed using magnetic driven, peristaltic, sinusoidal, or pneumatic pumps, such as diaphragm, reciprocating, plunger, piston or high-pressure pneumatic pumps.

Figure 4:
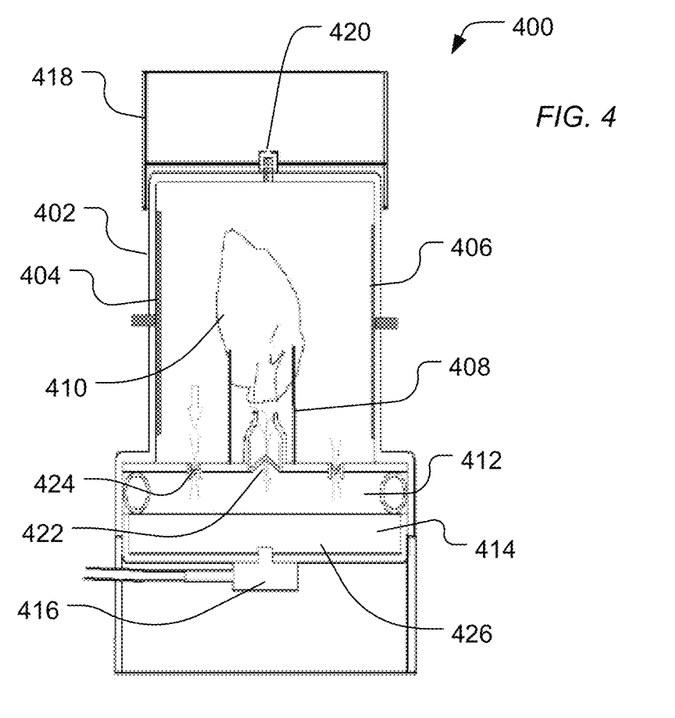
FIG. 4 includes an illustration of an exemplary electrophoretic decellularization device.

Turning to FIG. 4, an electrophoretic decellularization device 400 includes a container 402, in which at least two electrodes 404 and 406 are disposed. A tissue support 408 supports a tissue sample 410 between the at least two electrodes 404 or 406. The electrophoretic decellularization device 400 can also include a degassing or pressure release valve 420 and a capture container 418 to capture gas escaping through the degassing valve 420.

When the decellularization composition is a liquid, a liquid can be circulated using a pump 426 and valves 422 and 424. For example, the pump 426 can include a fluid chamber 412, a diaphragm 414 and a pressure source 416. The pressure source 416 can change pressure to drive the diaphragm 414 to push fluid from the chamber 412 through an outlet valve 422 positioned under the tissue support 408. Pressure can be removed from the diaphragm 414 and fluid can be drawn from the chamber 402 through outlet valve 424.

Alternatively, the decellularization composition can be provided by perfusion through the vascular system of the organs. In another alternative, the decellularization composition can be provided by direct injection, such as through a cannula or needle. For any of the circulation method, the direct injection method, or the perfusion method, the illustrated pump 426 can be replaced with a magnetic driven, peristaltic, sinusoidal, or pneumatic pump, such as a diaphragm, reciprocating, plunger, piston or high-pressure pneumatic pumps.

In operation, a tissue sample 410 is placed on support 408 within the chamber 402. A decellularization composition is provided to the chamber 402 to contact the electrodes 404 and 406 and tissue sample 410. Electrodes 404 or 406 can be sized to cover at least 60% of the projected area the tissue sample 410. In example, the decellularization composition is a buffered liquid solution having a pH in a range of 6.0 to 8.5. Further, the decellularization composition can include a surfactant, such as an anionic surfactant.

A voltage potential can be applied across the electrodes 404 or 406 using an external power source. In an example, the power source provides a constant voltage potential across the electrodes 404 or 406. In a further example, the power source can provide a constant current between electrodes 404 or 406. In an additional example, the power source can provide an oscillating voltage potential across the electrodes 404 and 406, such as an alternating voltage potential across the electrodes 404 and 406. In a further embodiment, the power source can provide an oscillating voltage potential across electrodes 404 and 406 with a constant bias.

While the voltage difference is applied across electrodes 404 or 406, a pump can be activated to provide a decellularization composition through the inlet valve 422 and to draw the decellularization composition through outlet valves 424. In such a manner, the decellularization composition can be circulated. Alternatively, the decellularization composition can be perfused through vasculature of the tissue sample. While the decellularization composition is illustrated as flowing in and out of a single diaphragm pump, alternatively, the decellularization composition can be drawn from the electrophoretic decellularization device 400, filtered, buffered, and resupplied to the chamber 402. In particular, decellularization can be performed for 1 hour to 790 hours, such as 1.5 hours to 360 hours, or 2 hours to 240 hours. For example, the decellularization can be performed in not greater than 300 hours, such as not greater than 250 hours, not greater than 200 hours, or not greater than 150 hours. The temperature during decellularization can be not greater than 35 C, such as not greater than 30 C, not greater than 28 C, or not greater than 26 C. In particular, the temperature is at least 15 C.

Optionally, the tissue holder 408 can rotate the tissue sample 410 by at least 90°. For example, the tissue holder 408 can rotate the tissue sample 410 by at least 180°. Alternatively, the electrodes 404 or 406 can be rotated around the tissue sample 410 by at least 90°, such as at least 180°. In a further alternative example, the electrophoretic decellularization device 400 can include additional electrodes. For example, the electrophoretic decellularization device 400 can include at least four electrodes surrounding the tissue sample 410. Each opposing pair of electrodes can be activated with a relative electric potential that is either constant, oscillating, or both.

In particular, the decellularization time is inversely proportional to the electrode surface area, electrode potential, decellularization strength of the solution and directly proportional to the amount of tissue, and distance between the electrodes. As such, $$Td \text{ is proportional to} (Vt \times De)/(Ae \times Pe \times Ss)$$

wherein, Td is the decellularization time, Vt is the tissue volume, De is the distance between electrodes, Ae is the area of electrodes, Pe is the electric potential across the electrodes, and Ss is the surfactant strength Once decellularization is complete, the decellularized tissue matrix can be removed from the electrophoretic decellularization device 400. Such a tissue matrix can be washed, sterilized, treated, and repopulated with cells. For example, cells from the patient can be used to repopulate the decellularized tissue matrix in vitro. In an alternative example, the decellularized tissue matrix can be implanted into a patient and the patient's cells can repopulate the decellularization tissue matrix in vivo.

Figure 6:
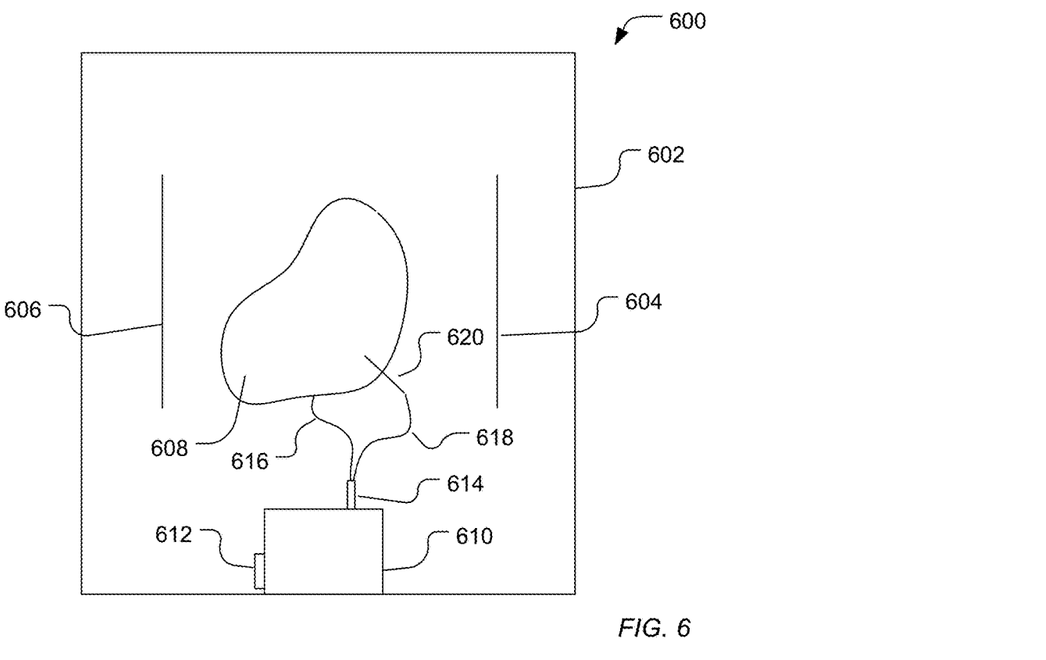
FIG. 6 includes an illustration of an exemplary electrophoretic decellularization device.

In a further example, the electrophoretic decellularization device, such as the device 400, can further include a perfusion pump and one or more conduits connected to the perfusion pump to provide a decellularization solution into the tissue. For example, FIG. 6 illustrates a device 600 that includes a container 602 and a tissue sample 608 disposed between two electrodes 604 and 606. The device 600 also includes a perfusion pump 610 having an inlet 612 and one or more outlets 614. As illustrated, the perfusion pump 610 can be disposed in the container 602 and decellularization fluid can be collected by the inlet 612 and pumped through the outlet 614. Alternatively, the perfusion pump 610 can be external to the container 602 and can receive decellularization solution from the container 602 through an inlet tube or can obtain decellularization solution from an external source. In a further example, the decellularization solution or composition pumped through the perfusion pump 610 can be different than the decellularization solution or composition within the container.

One or more conduits, such as tubes or hoses, can be connected to the outlet 614 of the perfusion pump 610. For example a tube 616 can be connected to the outlet 614 at one end and can be connected to the tissue 608 at the other end by suture, cannulation, or another mechanism to a vascular structure of the tissue 608. In another example, a tube 618 can be connected to the outlet 614 and can be connected to a needle 620 to inject decellularization solution into the tissue 608. In a further example, a tube can be connected to the outlet 614 and to a perfusion tube disposed within the tissue. A perfusion tube permits decellularization solution to permeate the tube walls and enter the tissue. An exemplary perfusion tube includes a woven tube structure or stent-like structure.

In a particular example, the chamber combines an approximately uniform electric field potential across the tissue with fluid circulation resulting in efficient decellularization of xenogeneic muscle tissue of various volume, shape and weight. The resulting extracellular matrix (ECM) can transmit physiologically relevant forces to tendons, providing a degradable collagen-based platform for progenitor cell differentiation to muscle, porosity for vascularization, or versatility to customize delivery of growth factors, cytokines and chemokines to improve regeneration. Large volume EMC scaffolds produced by the electrophoretic decellularization device can have the appropriate pore sizes to accommodate vasculogenesis to support muscle regeneration, can possess the biomechanical integrity of muscle, can remove antigens that causes tissue graft rejection, and can have a vascular and nerve network for transplant and regeneration into functional skeletal muscle tissue in areas with large soft tissue injuries and loss.

Exemplary ECM tissue derived from xenogeneic muscle tissue can have desirable properties for tissue regeneration. For example, the ECM tissue can be devoid of muscle cellular protein (<0.1% as evidenced by SD S-PAGE electrophoresis which is less that 50 ng in 50 microg loading), have appropriate porosity for cell and vascular growth (pore size in the range 10 to 500 microns as shown by SEM), have sufficient tensile strength to transmit mechanical force observed in muscle (maximum load prior to failure 15-30 N based on tensile testing), have appropriate stiffness for cellular differentiation into muscle (1-25 kPa based on AFM or tensile testing), not illicit an immune response in vivo (low grade response based on pathologic evaluation of H&E stained sections), support muscular growth in vivo (evidence of MyoD staining in implanted ECM and centralized nuclei in regenerating muscle), degrade over time in vivo (evidence of collagen remodeling based on picosirus red staining and polarized light microscopy), or any combination thereof.

More generally, an ECM supports a number of functions beyond simple structural support including controlling the chemical and mechanical microenvironment, sequestering and presenting active growth factors, and mediating cell-cell contact. Once formed, the ECM can be repopulated with stem cells.

Stem cells include a population of cells that has the ability to self-renew and to differentiate into one or more specialized mature cell types. The classification of stem cells is often dependent on their species and tissue of origin and their differentiation potential into mature cell type(s). Stem cells isolated from various sources can vary in their differentiation capacity or pluripotentiality. Such differentiation capacity is thought to be an indication of cellular differences in the organisms, the ontogenic stage of the stem cell or the environmental conditions to which the stem cell is exposed. Two primary groups of stem cells have been defined, to date. The first group, embryonic stem cells (ESCs), is believed to have an indefinite replicative capacity and the ability to generate somatic cells of the body. The second population of stem cells is denoted as adult stem cells, which have been characterized from adherent and non-adherent fractions of bone marrow, adipose tissue, as well as specific organs. Such cells can be expanded in clinically relevant proportions and can be autologous. Stem cells can be isolated from a patient's own bone or adipose and prepared for infusion within 1-2 hours.

The transmission of mechanical force by extracellular matrix (ECM) generally regulates cellular responses, extending from basic processes of engraftment, such as motility and spreading, to differentiation. When myotubes are grown on ECM substrates, they striate only on compliant surfaces that mimic the normal force transmission found in muscle. Specific matrix stiffness can lead to specification of a specific lineage, including neuronal, muscle or osteoblasts. Such specification results in stable programming of the cells that cannot be reprogrammed by altering either the mechanical or cytokine environment. As such, stem cells can be preconditioned for tissue engineering.

EXAMPLES

A decellularized ECM is prepared from rat plantaris muscle in the device illustrated in FIG. 4. Mass spectrophotometric analysis of the isolated decellularized ECM demonstrates that the ECM is composed primarily of collagen, with trace amounts of actin, and desmin. The tensile strength of the ECM oriented along the long axis of decellularized rat plantaris muscle is determined on an Intron tensiometer and found to be between 35 and 45 kPa.

The ECM is sutured into a defect area of the Lateral Gastrocnemius (LG) of a rat and withstands forces of maximal tetanic tension from 0-56 days post surgery. Removal of a portion of the rat (LG) amounting to a mean mass of 286.6±12 mg (LG) initially decreases the maximal tetanic force to 85% of that of the control (LG). With the ECM sutured into the defect area at day 0 the force remained at 85% of maximal force. After 28 days the muscle regains an average of 65 mg of mass and a maximal tetanic force of 93% of control (LG). The disproportional increase in maximal tetanic force of approximately 50% relative to a 22-25% restoration of mass is attributed to the ECM serving as a scaffolding for the transmission of force.

The implantation of an ECM serves as a scaffold to fill the void in the muscle. Cosmetically, the repaired LGAS appears identical to the control muscle, but that there is limited restoration of mechanical force. Histological evaluation of the ECM demonstrates that myogenesis occurs in a limited manner inward from the portions of cut muscle into the ECM roughly 2-3 mm. The core of the 1×1 $cm^2$, approximately a section of 30-40 $mm^2$, however remains a hypoxic core of the ECM, exhibiting limited vasculogenesis and myogenesis. Functionally, the contractile force of the damaged muscle, following implantation of the ECM, remains stable over 6 weeks, but does not improve. Stimulation of the muscle via tibial nerve activation or through direct electrical stimulation of the muscle demonstrates a lack of functional innervation of the regenerated myofibers.

The example is repeated by creating a defect with ECM fitted and sutured into the deficit space, but infused with bone marrow mesenchymal cells (BMSCs) into the ECM after one week of recovery. BMSCs are isolated and expanded in culture and analyzed for cell surface markers by FACS analysis. Over 99% of cells are positive for CD90 and negative for CD45, CD34, and CD146. Approximately 1.5 million BMSCs are infused into the ECM in three separate injections in a total volume of 0.3 mL. The portion of the LGAS removed to create the defect is 223±5 and 228±6 mg wet weight for ECM-ONLY and ECM-CELL, respectively, which is nearly 20% of the mass of the LGAS. Stimulating the LGAS via the tibial nerve is used to assess tetanic tension at 14, 28, and 42 days of recovery in situ. The LGAS demonstrates significant increases in mechanical force and restoration of muscle mass, between 28 and 42 days. The maximal isometric tetanic force produced by the LGAS of the ECM-CELL group is significantly higher after 42 days of recovery than after 14 or 28 days of recovery (p<0.05). Without cells, but with implanted ECM, no functional recovery of the LGAS occurs over 42 days.

Specific tension (SPo), the maximal tetanic force per unit of cross-sectional area, of the LGAS in the ECM-CELL group increases significantly relative to the contralateral from 77%±12 at 14 days of recovery to 94%±9 at 42 days of recovery (p<0.01). The mass of the LGAS increases to 90% of control resulting in 85% of maximal force at the tendon.

The full repair of a large defect in a skeletal muscle results from the growth of myofibers, but it also utilized blood vessel integration and nerve innervation of the myofibers. The muscle fibers increase between 28 and 42 days. The ECM is divided into thirds with the top third closest to the origin of the LGAS and the bottom third coming from that portion closest to the Achilles tendon. Slides are stained with Trichrome in which the blue represents connective tissue (ECM) and the deep orange represents muscle cells. The insets in the micrographs represent immunofluorescent staining for desmin (green) and myogenin (red). The muscle specific protein desmin and the transcription factor myogenin are used to identify myofibers at different stages of regeneration, within the ECM implant. The number of desmin positive fibers per square millimeter is significantly higher after 42 days of recovery in the ECM-CELL group compared to all other groups (p<0.05). Significantly more myogenin positive nuclei and desmin positive fibers are found in the MSC-seeded ECMs at 28 and 42 days of recovery.

Example 2

Tissue is decellularized using electrophoresis in a sodium dodecyl sulfate (SDS) solution to demonstrate the speed and efficiency of tissue decellularization. In contrast to methods using agarose gel, decellularization in a SDS solution decellularizes a cardia valve of 6 gm to an ECM in less than 24 hours of time.

The tissue decellularized samples are also tested microscopically and with gel electrophoresis. Stained cross-sections of the muscle tissues exposed before and after electrophoresis decellularization demonstrates that electrophoresis decellularization can produce a bio-scaffold which has removed cellular materials including cell walls, immunogenetic proteins, and other cellular residues. The electrophoresis gel exhibits little or no protein after electrophoresis decellularization as compared to whole muscle.

Example 3

PEGylated fibrin is utilized for therapeutic purposes in a muscle injury model involving the excision of a large portion of the lateral gastrocnemius and the replacement of the excised portion with a decellularized ECM. Muscle defects treated with either an ECM alone or ECM+PEGylated fibrin exhibit at least a 40% improvement in lateral gastrocnemius function with ECM+PEGylated fibrin exhibiting greater improvement over ECM alone after 56 days of recovery.

Example 4

A fresh cadaveric porcine gastrocnemius is harvested. The popliteal artery is severed during the recovery, leaving the branch supplying the medial muscle bundle intact. This artery is cannulated and flushed with heparinized saline until venous outflow is clear. The muscle is placed horizontally into a support with the dorsal side downward.

The support is lowered into a 2% solution of liquid pH adjusted detergent in deionized water within the decellularizing chamber. The tissue is positioned between two aluminum electrodes 10"×8" bent to conform to the curvature of the chamber. The popliteal artery branch catheter is attached to the perfusion element. The system is sealed and is purged of air with additional deionized water. The fluidic perfusion system is initiated, providing a flow of approximately 20 ml/min. Decellularization is conducted at room temperature at 50 mA. The initial voltage is measured at 3.5V.

During the initial 20 hours of decellularization, muscle weight drops by approximately 1 gram/hour. After 20 hours the solution is replaced by 1% SDS. The popliteal artery branch is inadvertently torn and the stump is found for re-catheterization. Decellularization continues for another 24 hours with solution circulation only.

Decellularizing solution is replaced after 56, 65, 114, 50, 72, 24, 23.5, 23.5, and 18 hours respectively. At each interval, the tissue is weighed. Initially the muscle loss of 1 gm/hr for the first 20 hours is observed. After 150 hours the muscle gains 100 g from the start of the process. The weight gain may be caused by deposition of detergent(s) driven into the ECM by the perfusion and electrophoresis process. Another possible explanation is the accumulation of the protein by-products resulting from electrophoresis that are bound and lodged in the ECM and are hindered from being perfused out into the decellularization solution.

Figure 7:
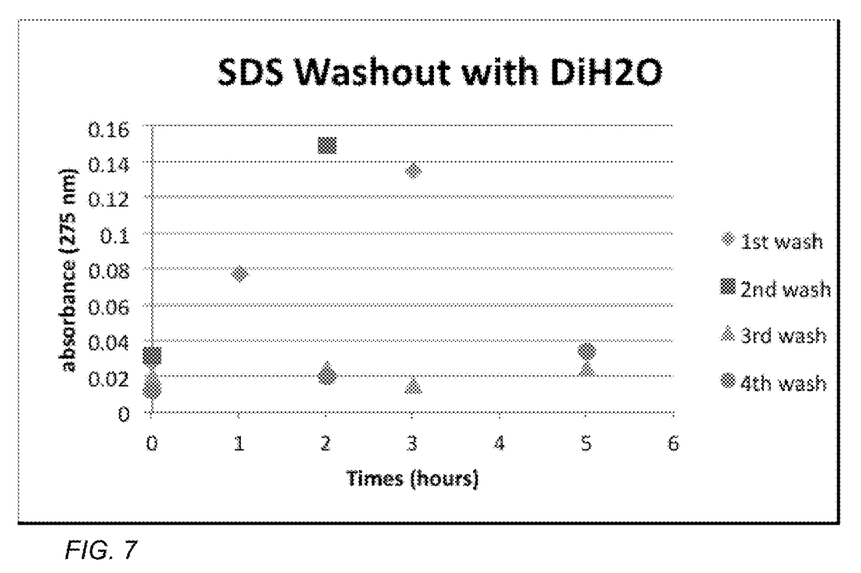
FIG. 7 includes a graph illustrating surfactant washout performance.

To test this hypothesis, the ECM is subjected to a washout with deionized $H_2O$ at 400 mA electrophoretic current. Voltage drops within two hours and remains relatively constant thereafter. This observation suggests that a substantial amount of detergent migrates out of the tissue into the wash solution. Spectrophotometric analysis of fresh decellularization detergent solution shows a major absorbance peak at 270 mm After a period in decellularization, the peak at 270 nm is more pronounced, however at a lower absorbance. This peak may represent a detergent/tissue component complex. FIG. 7 illustrates the change in absorbance following multiple washouts. In the first two washouts, a significant increase in the SDS:cell material complex occurs in the first 2 hours. The subsequent washouts show little of the complex in the Di-H2O, suggesting that within 4 hours the ECM is clear. This finding suggests that 6 hours of washout may be sufficient to remove the detergent/tissue complexes Example 5

Figure 8:
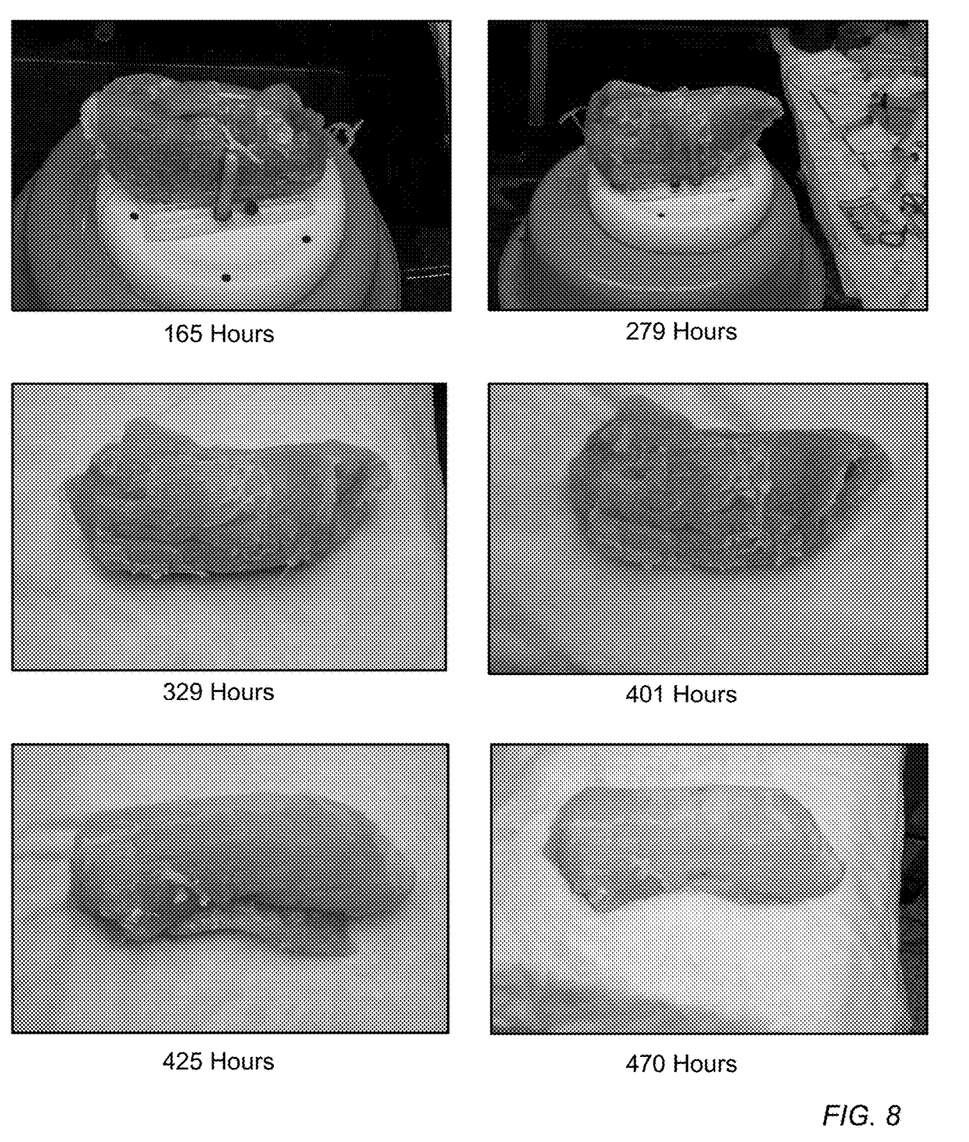
FIG. 8 includes pictorial illustrations of treated tissue.

Porcine Muscle 500 g: FIG. 8 depicts progressive stages of decellularization of 500 gms of porcine muscle using the decellularization device. The ECM changes from a redish/pink color to a mostly white translucent material. Qualitatively, extensive decellularization occurs on a large volume mass of muscle tissue using the decellularization device developed.

Example 6

Porcine Muscle 915 and 547 g: Additional large volume porcine muscle tissue is decellularized using the decullarization device.

Figure 9A:
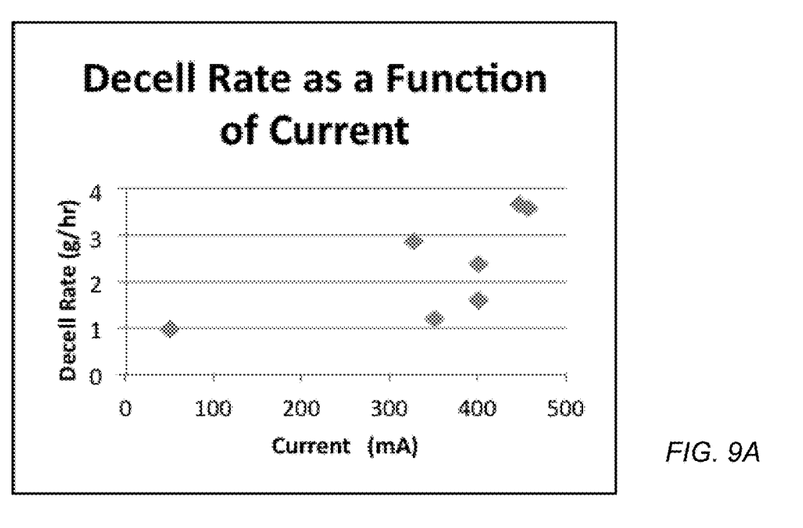
FIG. 9A and FIG. 9B include graphs illustrating decellularization rates relative to parameters.
Figure 9B:
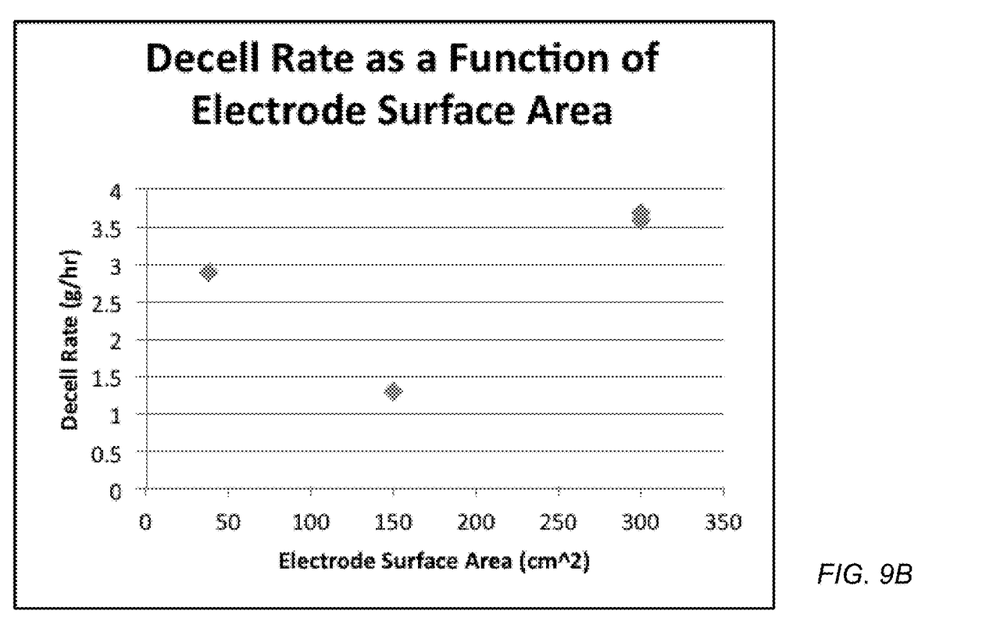

Porcine skeletal muscles 915 g and 547 g are decellularized at a constant electrode surface area and varying applied currents. The decellularization solution is a mixture of water, sodium alkyl sulfonate, sodium alkyl ethoxylate sulfonate amine oxide, ethyl alcohol, and sodium lauryl benzene sulfonate. After 24 hours of decellularization, the tissue is removed from the chamber, washed, patted dry and weighed. FIG. 9 illustrates that the higher currents significantly increase the decellularization rate. Larger electrode surface areas correlate with lower internal resistances, resulting in reduced heating of the solution including the ECM. An electrode area of 300 cm$^2$ operating at a current of 400 mA generates an amount of heat that is dissipated through the decellularization chamber during operation. Temperatures range from 22 C to 24 C. An electrode area of 150 cm$^2$ at 400 mA generates sufficient heat to bring the decellularization solution to 32.5 C within 30 minutes. Either reduction of operating current or heat removal maintains the system below 25 C. It appears that electrode surface areas of 300 cm$^2$ at a decellularization current of 450 mA can decellularize a full thickness muscle of 1 to 2 pounds (450 to 900 g) within 122 to 243 hours or 5-10 days while maintaining temperatures below 25 C.

Figure 10A:
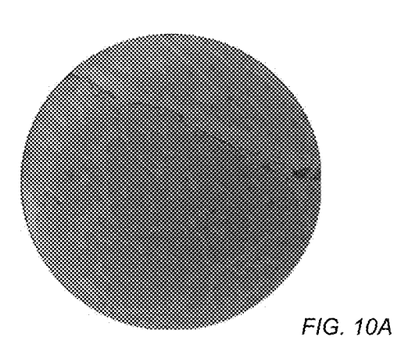
FIG. 10A, FIG. 10B, and FIG. 10C include pictorial illustrations of stained tissue samples.
Figure 10B:
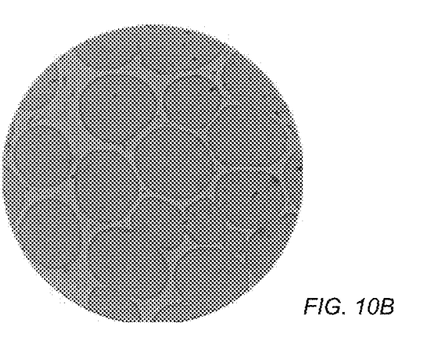
Figure 10C:
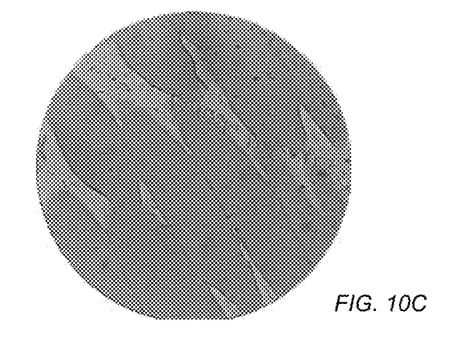

Decellularized porcine skeletal muscle is stained with haemotxylin and eosin. The ECM is clear and easily allows light to pass through. The micrograph at 100× magnification shows what appears to be both longitudinal and cross-sectional profiles of the collagen muscle matrix (FIG. 10A). The internal volumes appear to be void of cellular material. The same muscle is magnified at 400× the cross-sectional and longitudinal matrices confirm the absence of cellular material (FIG. 10B and FIG. 10C).

Example 7

Porcine Muscle 63, 270 & 790 gm: Decellularization of porcine muscle (63 g, 72 cm$^3$) is carried out at a mean current of 252±108 mA and a mean voltage of 35±12V using a detergent, with no perfusion through the muscle mass. The temperature of 23±4 C is maintained throughout the decellularization period. Decellularization occurs over 57 hours or 2.5 days. Final weight of the tissue is 133 g and a volume of 122.5 cm$^3$, indicating significant accumulation of decellularization solution within the ECM. Higher decellularization currents result in significant bath warming that utilized cooling with externally applied cold packs and fan directed air flow around the decellularization canister.

After a 135 minute washout with deionized water at 89±44 mA and 152 V significant washing out of decellularization solution from the muscle resulted in a drop in weight to 94 g. During the washout period the decellularization current starts at 51 mA and increases to 166 mA, suggesting a significant decrease in solution resistance. The finding is consistent with the notion that detergent was diffusing from the ECM. The findings also indicate additional washout can be used to achieve complete removal of the detergent solution. Temperature during decellularization is 25±2° C. Haemotxylin and eosin stain of cross-sections and longitudinal sections of the ECM appear to show engorged matrix cells presumably the result of incomplete detergent washout.

Figure 11:
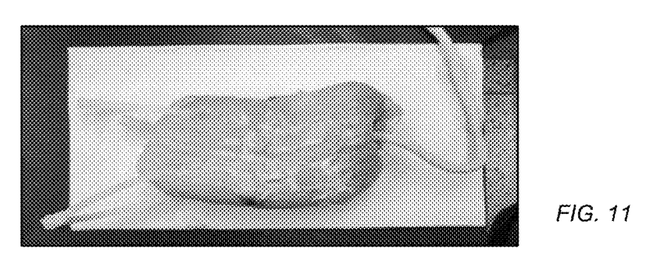
FIG. 11 includes a pictorial illustration of decellularized tissue.

The 270 g porcine gastrocnemius is decellularized using a 0.635 cm diameter Dacron woven tube introduced through the muscle's central axis for perfusion. The SDS (1%) solution is used as the decellularization solution with a flow rate of 30 ml/min. Decellularization current is maintained at approximately 250 mA at 20V. The temperature is maintained at 25.5 C. Decellularization proceeds for 140 hours. FIG. 11 depicts the level of decellularization after 140 hours.

A portion of a porcine thigh muscle weighting 790 g with intact vasculature is harvested and is decellularized. The muscle is prepared by catheterizing a branch of the femoral vein and flushing with heparinized saline retrograde until no blood is observed draining from the arterial vessels. Several liters of de-ionized water are flushed through the muscle and is then stored at −20 C. The decellularized ECM shows complete removal of cellular components.

Example 8

Porcine muscle samples of sizes ranging from 0.5" to 2.0" in diameter and varying in length from 2.0" to 7.0" in length. The muscle tissue to be decellularized is inserted into a decellularization chamber.

The rates of elution of protein from the muscle are measured as the muscle undergoes decellularization by gel densitometry. The protein quantification is done on gels since the SDS, which is part of the decellularization solution, interferes with the normal BioRad (Bradford) protein assays, which is based upon the binding of Comassie Blue to the proteins. Utilizing the digital gel scanner and loading it with albumin of varying concentrations, a linear relationship is determined. The quantification of the protein is done utilizing gel electrophoresis so that one can overcome the interference due to the Comassie blue binding with the SDS.

The elution of protein from the sample remains constant and the solution does not seem to be saturating. A number of protein samples are taken at different time intervals on each day (i.e. Day 1, Day 2, and Day 3). From these protein rates of elution, the total weight of protein eluted to be 12.17 g from a starting muscle weight of 14.49 gm giving an ~84% (w/w) of protein that is eluted from the resulting ECM.

Example 9

Prior to implantation, an ECM has a tensile strength (25-30 N) and stiffness (10-35 kPa). The ECM is implanted into the lateral gastrocnemius of a rats. The strength of the isolated ECM is tested in vitro and stretched to failure. The protein concentrations released from the muscle a determined by taking the change in concentration of protein as measured by gel densitometry.

Cellular Protein Analysis of the ECM: By using a digital gel scanner and loading it with albumin of varying concentrations, a linear relationship is determined. A yield of 0.14 mg/ml of protein in a 600 mg piece of ECM using the UT decellularization chamber design is determined. The ECM is homogenized in 3 ml of buffer, run on a gel and imaged. The intensities of the serial dilutions are logged and are plotted on a graph, linear regression lines are calculated. Using the equation of the linear regression line of known sample concentrations, the concentration of unknowns is determined using the intensity of the sample(s). The decellularized ECM has substantially all cellular protein removed.

Sprague Dawley Rat Implant (Immune Response): a portion of the porcine ECM produced is implanted into five (5) Sprague Dawlety rats. A deficit of approximately 250 mgm is created in the lateral gastrocnemius and after only 6 weeks (42 days) post-implant the leg shows no sign of an altered gait while walking on a treadmill. The rat shows no signs of infection or rejection. Testing for antigenetic response provides no indications of any adverse response.

The implantation of the ECM into the rat defect model demonstrates good contractile strength at 42 days after ECM implantation without progenitor cell infusion. Based on tissue sections of the ECM that are frozen and made into histological and immunohistological slides on three regions, the porcine muscle implantation into the rat demonstrates regeneration. The cross-sectional slices of the LGAS after 42 days shows significant regeneration of the muscle. The cross-sectional slices also indicate major restoration of both vascular (angiogenesis) and innervation.

The LGAS muscle were taken out of the rat(s) after 42 days. The leg muscles appear normal and the margins/borders of the defect area are difficult to identify Myotube Analysis: Myoblasts, isolated from skeletal muscle of the rat, are plated into 24 well plates. The bottoms of the well plates are coated with sections of ECM derived from the porcine muscle. The myoblasts form myotubes with several fibers of skeletal muscle forming and contracting in the differentiation media. A histogram analysis of the myofiber density along the entire length of the implanted ECM shows significant regeneration and regrowth of myofiber along the length of the LGAS.

Tensile Strength & Force Measurements: Porcine implants are implanted for 42 days. The implants of the ECM into the rat defect model demonstrates contractile strength without additional progenitor cell infusion. The Table summarizes the regenerated ECM muscle implant results. The removal of 250 mgm of muscle resulted in 57% regeneration of the muscle loss ([1416–1274 mgm]/240 mgm).

Force measurement of the LGAS is performed by attaching the muscle to a lever arm of a dualmode servomotor (model 310 B; Aurora Scientific, Aurora, ON, Canada). The muscle is stimulated to contract by a stimulator (Model 2100; A-M Systems, Calsborg, Wash.) with leads applied to the tibial nerve.

Force restoration is found to be approximately 64% and 68% tension. The regenerative capability of the implanted ECM is demonstrated with restoration of both vascular (angiogenesis) and innervation In a first aspect, a device for decellularizing a tissue includes a container, first and second electrodes disposed within the container and defining a space between the first and second electrodes to receive the tissue, a perfusion pump, and a conduit connected to the perfusion pump to transport a decellularization solution from the pump into the tissue.

In an example of the first aspect, the surface area is at least 60% of the projection area. For example, the surface area is at least 75% of the projection area, such as at least 90% of the projection area.

In a further example of the first aspect and the above example, the first electrode is coated with a first corrosion-resistant conductive material. For example, the corrosion-resistant conductive material includes platinum, gold, silver, or a combination thereof. In another example, the corrosion-resistant conductive material includes a conductive ceramic material. In a further example, the corrosion-resistant conductive material includes a conductive polymeric material. In a particular example, the second electrode is coated with a second corrosion-resistant conductive material. For example, the first corrosion-resistant conductive material is the same as the second corrosion-resistant conductive material. In an additional example, the first corrosion-resistant conductive material is different than the second corrosion-resistant conductive material.

In another example of the first aspect and the above examples, the device further includes a power source electrically coupled to the first and second electrodes. For example, the power source is to provide a constant voltage difference between the first and second electrodes. In another example, the power source is to provide an oscillating voltage difference between the first and second electrodes. In a further example, the power source is to provide an oscillating voltage difference with a voltage bias between the first and second electrodes.

In an additional example, the device further includes a decellularization composition disposed within the container and in contact with the first and second electrodes. For example, the decellularization composition includes a surfactant. In an example, the surfactant is an ionic surfactant. In particular, the ionic surfactant is an anionic surfactant. In another example, the ionic surfactant is a cationic surfactant. In an additional example, the decellularization composition is buffered to a pH in a range of 6.5 to 8.5, such as to a pH in a range of 7.0 to 8.0. In a further example, the decellularization composition is a liquid solution. Alternatively, the decellularization composition is a hydrogel.

In a second aspect, a method of decellularizing a tissue includes disposing the tissue within a device. The device includes a container, first and second electrodes disposed within the container and defining a space between the first and second electrodes to receive the tissue, a perfusion pump, and a conduit connected to the perfusion pump to transport a decellularization composition from the pump into the tissue. The method further includes disposing the decellularization composition within the container to surround the tissue and contact the first and second electrodes, applying an electric potential across the first and second electrodes, and perfusing the decellularization composition into the tissue.

In an example of the second aspect, the decellularization composition is a liquid solution. In another example, the decellularization composition is a hydrogel.

In another example of the second aspect and the above example, the decellularization composition includes a surfactant. For example, the surfactant is an ionic surfactant. In an example, the ionic surfactant is an anionic surfactant. In another example, the ionic surfactant is a cationic surfactant.

In a further example of the second aspect and the above examples, the decellularization composition is buffered to a pH in a range of 6.5 to 8.5, such as to a pH in a range of 7.0 to 8.0.

In an additional example of the second aspect and the above examples, the surface area is at least 75% of the projection area.

In another example of the second aspect and the above examples, the device further includes a power source electrically coupled to the first and second electrodes. For example, the method can further include providing with the power source a constant voltage difference between the first and second electrodes. In another example, the method further includes providing with the power source an oscillating voltage difference between the first and second electrodes. In an additional example, the method further includes providing with the power source an oscillating voltage difference with a voltage bias between the first and second electrodes.

In a third aspect, a device for decellularizing a tissue includes a container, first and second electrodes disposed within the container and defining a space between the first and second electrodes to receive the tissue, the first and second electrodes including a surface of a corrosion-resistant conductive material, and a tissue support to position the tissue within the space.

In an example of the third aspect, the corrosion-resistant conductive material includes platinum, gold, silver, or a combination thereof. In another example, the corrosion-resistant conductive material includes a conductive ceramic material. In an additional example, the corrosion-resistant conductive material includes a conductive polymeric material.

In a further example of the third aspect and the above examples, the second electrode is coated with a second corrosion-resistant conductive material. In another example, the first corrosion-resistant conductive material is the same as the second corrosion-resistant conductive material. In an additional example, the first corrosion-resistant conductive material is different than the second corrosion-resistant conductive material.

In a fourth aspect, a method of decellularizing a tissue includes disposing the tissue within a device. The device includes a container, first and second electrodes disposed within the container and defining a space between the first and second electrodes to receive the tissue, the first and second electrodes including a surface of a corrosion-resistant conductive material, and a tissue support to position the tissue within the space. The method further includes disposing a decellularization composition within the container to surround the tissue and contact the first and second electrodes and applying an electric potential across the first and second electrodes.

In a fifth aspect, a method of decellularizing a tissue includes disposing the tissue within a device. The device includes a container, first and second electrodes disposed within the container and defining a space between the first and second electrodes to receive the tissue, and a tissue support to position the tissue within the space. The method further includes disposing a decellularization composition within the container to surround the tissue and contact the first and second electrodes, the decellularization composition buffered to a pH in a range of 6.5 to 8.5, and applying an electric potential across the first and second electrodes.

In an example of the fifth aspect, the decellularization composition is a hydrogel. In another example of the fifth aspect, the decellularization composition is a liquid solution. For example, the decellularization composition includes a surfactant. In an example, the surfactant is an ionic surfactant. In a further example, the ionic surfactant is an anionic surfactant. In an additional example, the ionic surfactant is a cationic surfactant. In a particular example, the decellularization composition is buffered to a pH in a range of 7.0 to 8.0.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive- or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method of decellularizing a tissue, the method comprising:
    disposing the tissue within a device, the device comprising:
        a container;
        first and second electrodes disposed within the container and defining a space between the first and second electrodes to receive the tissue; and
        a perfusion pump;
        a conduit connected to the perfusion pump to transport a decellularization composition from the pump into the tissue; and
        a permeable perfusion tube connected to the conduit and inserted into nonvascular portions of the tissue;
    disposing the decellularization composition within the container to surround the tissue and contact the first and second electrodes;
    applying an electric potential across the first and second electrodes; and
    perfusing the decellularization composition through the permeable perfusion tube and into the tissue.

2. The method of claim 1, wherein the decellularization composition is a liquid solution.

3. The method of claim 1, wherein the decellularization composition is a hydrogel.

4. The method of claim 1, wherein the decellularization composition includes a surfactant.

5. The method of claim 4, wherein the surfactant is an ionic surfactant.

6. The method of claim 5, wherein the ionic surfactant is an anionic surfactant.

7. The method of claim 5 wherein the ionic surfactant is a cationic surfactant.

8. The method of claim 1, wherein the decellularization composition is buffered to a pH in a range of 6.5 to 8.5.

9. The method of claim 8, wherein the decellularization composition is buffered to a pH in a range of 7.0 to 8.0.

10. The method of claim 1, wherein a surface area of the first or second electrode is at least 75% of a projection area.

11. The method of claim 1, wherein the device further includes a power source electrically coupled to the first and second electrodes.

12. The method of claim 11, further comprising providing with the power source a constant voltage difference between the first and second electrodes.

13. The method of claim 11, further comprising providing with the power source an oscillating voltage difference between the first and second electrodes.

14. The method of claim 11, further comprising providing with the power source an oscillating voltage difference with a voltage bias between the first and second electrodes.

15. A method of decellularizing a tissue, the method comprising:
   disposing the tissue within a device, the device comprising:
      a container;
      first and second electrodes disposed within the container and defining a space between the first and second electrodes to receive the tissue;
      a tissue support to position the tissue within the space;
      a perfusion pump;
      a conduit connected to the perfusion pump to transport a decellularization composition from the pump into the tissue; and
      a permeable perfusion tube connected to the conduit and inserted into nonvascular portions of the tissue;
   disposing a decellularization composition within the container to surround the tissue and contact the first and second electrodes, the decellularization composition buffered to a pH in a range of 6.5 to 8.5; and
   applying an electric potential across the first and second electrodes.

16. The method of claim 15, wherein the decellularization composition is a hydrogel.

17. The method of claim 15, wherein the decellularization composition is a liquid solution.

18. The method of claim 15, wherein the decellularization composition includes a surfactant.

19. The method of claim 18, wherein the surfactant is an ionic surfactant.

20. The method of claim 19, wherein the ionic surfactant is an anionic surfactant.

* * * * *